United States Patent [19]

Cooper

[11] Patent Number: 4,772,694

[45] Date of Patent: Sep. 20, 1988

[54] CHIRAL 3-(1,2,5-TRISUBSTITUTED IMIDAZOLIDINONE) AZETIDINONE ANTIBIOTIC INTERMEDIATES

[75] Inventor: Robin D. G. Cooper, Indianapolis, Ind.

[73] Assignee: Eli Lilly and Company, Indianapolis, Ind.

[21] Appl. No.: 888,895

[22] Filed: Jul. 24, 1986

[51] Int. Cl.$^4$ .................. C07D 403/04; C07D 405/14; C07D 409/14; C07D 233/32

[52] U.S. Cl. .................................... 540/364; 548/337; 548/225

[58] Field of Search ........................................ 540/364

[56] References Cited

U.S. PATENT DOCUMENTS 4,166,816 9/1979 Gleason et al. .................. 260/239 A
4,200,572 4/1980 Gleason et al. .................. 260/239 A

OTHER PUBLICATIONS

Ernst et al, Chem. Abs. 93, 26367.
Soma et al, Chem. Abs. 82, 156034t.
Ikota et al., Heterocycles, vol. 22, No. 10, pp. 2227-2230, 1984.
Evans et al., Tetrahedron Letters, vol. 26, No. 32, pp. 3783-3786, (1985).
Evans et al., Tetrahedron Letters 26, pp. 3787-3790, (1985).

*Primary Examiner*—Mark L. Berch
*Attorney, Agent, or Firm*—William B. Scanlon; Leroy Whitaker

[57] ABSTRACT

2,5-Disubstituted oxazolidin-4-one-3-ylacetyl chlorides and 1,2,5-substituted imidazolidin-4-one-3-yl-acetyl chlorides function as chiral auxiliary moieties in the asymmetric cycloaddition with aldimines to provide cis-azetidinones. The azetidinones are useful intermediates in the preparation of antibiotics.

16 Claims, No Drawings

CHIRAL 3-(1,2,5-TRISUBSTITUTED IMIDAZOLIDINONE) AZETIDINONE ANTIBIOTIC INTERMEDIATES

BACKGROUND OF THE INVENTION

This invention relates to intermediates for β-lactam antibiotic compounds. In particular, it relates to chiral azetidinone intermediates useful in the preparation of β-lactam antibiotics.

The ketene-imine cycloaddition process for the preparation of azetidinones has been previously studied. For example, D. A. Evans and E. B. Sjogren, *Tetrahedron Letters*, Vol. 26, No. 32, pp. 3783–3786, ibid pp. 3787–3790, and Ikota et al., *Heterocycles*, 1984, 22, 2227, have reported on the asymmetric preparation of azetidinones by the ketene-imine cycloaddition. Such studies are directed to the preparation of newer antibiotic substances not obtainable by natural means such as by fermentation. Intermediates having the correct chirality for the desired antibiotic would be valuable compounds useful in the preparation in non-classical β-lactam antibiotics.

SUMMARY 3-(2,5-Disubstituted imidazolidin-4-one-3-yl)-4-(substituted vinyl) and 4-protected carboxy-substituted cis-azetidinones and the corresponding 3-oxazolidin-4-one-3-yl azetidinones are obtained asymmetrically in the cycloaddition of aldimines and 2,5-disubstituted imidazolidin-4-one-3-ylacetyl chlorides or the corresponding oxazolidin-4-one-3-ylacetyl chlorides. The latter serve as chiral auxiliaries in the asymmetric preparation of the azetidinones. The azetidinones are intermediates useful for preparing known antibiotics.

DETAILED DESCRIPTION

The azetidinone compounds provided by this invention are represented by the following formula 1,

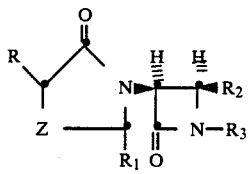

wherein Z is O or N-R' wherein R' is $C_1$-$C_4$ alkoxycarbonyl, benzyloxycarbonyl, Ar-substituted benzyloxycarbonyl; benzoyl or substituted benzoyl; R is $C_1$-$C_4$ alkyl, $C_1$-$C_4$ alkyl monosubstituted by hydroxy, protected carboxy, carbamoyl, thiobenzyl, $C_1$-$C_4$ alkylthio or protected amino, phenyl, substituted phenyl, naphthyl, substituted naphthyl or $C_1$-$C_4$ alkoxycarbonyl; $R_1$ is $C_1$-$C_4$ alkyl, $C_3$-$C_7$ cycloalkyl, phenyl, substituted phenyl, naphthyl, substituted naphthyl or $C_1$-$C_4$ alkoxycarbonyl; $R_2$ is $C_1$-$C_4$ alkoxycarbonyl, 2-(protected carboxy)ethyl, 4-(protected carboxy)butan-3-one or a group represented by the formula

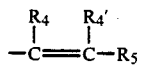

wherein $R_4$ and $R_4'$ independently are hydrogen or $C_1$-$C_4$ alkyl, $R_5$ is phenyl, naphthyl, m-$C_1$-$C_4$ alkoxyphenyl, furyl or protected carboxy; and $R_3$ is hydrogen, protected carboxymethyl, a ketal or thioketal derivative of a 1-(protected carboxy)propan-2-one-1-yl group or an NH protecting group.

The compounds represented by formula 1 are 3-(2,5-disubstituted oxazolidin-4-one-3-yl)azetidinones and 3-(2,5-disubstituted imidazolidin-4-one-3-yl)azetidinones wherein the 3-position heterocycle has two asymmetric centers. The heterocycle in the 3-position functions as a chiral auxiliary in the preparation of the azetidin-2-one (1) and is removed to provide the 3-aminoazetidinone of the desired chirality for antibiotics.

The compounds of the invention (1) are prepared via the so-called 2+2 cycloaddition of an oxazolidin-4-one-3-yl-acetyl chloride or the imidazolidin-4-one-3-yla-cetyl choride represented by the formula A

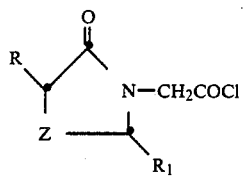

with an imine represented by the formula B

in the presence of a tertiary amine such as triethylamine.

The azetidin-2-one (1) is useful as an intermediate in the preparation of β-lactam antibiotic compounds as described hereinafter.

The terms used hereinabove in the definition of the compounds of the invention have the conventional meaning. For example, $C_1$-$C_4$ alkoxycarbonyl, refers to methoxycarbonyl, ethoxycarbonyl, propoxycarbonyl, t-butoxycarbonyl, and like straight and branched chain ester groups. The term Ar-substituted benzyloxycarbonyl refers to the benzyloxycarbonyl group wherein the phenyl ring is substituted by one or two of the same or different substituents such as $C_1$-$C_4$ alkyl, e.g. methyl or ethyl; $C_1$-$C_4$ alkoxy, e.g. methoxy or ethoxy; halogen, e.g. chloro or bromo; cyano, nitro, amino, mono- or di-($C_1$-$C_4$ alkyl)amino, e.g. dimethylamino or ethylamino; carbamoyl, or hydroxy. The term substituted benzoyl likewise refers to benzoyl substituted by one or more of the same or different substituents such as $C_1$-$C_4$ alkyl, $C_1$-$C_4$ alkoxy, halogen, hydroxy, cyano, carbamoyl, amino, mono- or di($C_1$-$C_4$ alkyl)amino, $C_1$-$C_4$ alkylsulfonylamino or nitro. The term substituted phenyl also refers to mono- or di-substituted phenyl groups wherein the substituents can be those referred to above as substituents for benzoyl. Substituted naphthyl refers to the naphthyl group substituted by one or two of the same or different substituents such as $C_1$-$C_4$ alkyl, $C_1$-$C_4$ alkoxy, halogen, cyano, nitro, amino, mono-or di-($C_1$-$C_4$ alkyl)amino, hydroxy or carbamoyl.

The terms protected carboxy and protected carboxymethyl refer to the carboxy group and the carboxy group of carboxymethyl protected or blocked by a conventional protecting group commonly used for the temporary blocking of the acidic carboxy. Examples of such groups include lower alkyl, e.g. t-butyl, halo-substituted alkyl, e.g. 2-iodoethyl, and 2,2,2-trichloroethyl, benzyl and substituted benzyl, e.g. 4-methoxybenzyl, and 4-nitrobenzyl, diphenylmethyl, alkenyl, e.g. allyl, trialkylsilyl, e.g. trimethylsilyl, and t-butyldiethylsilyl and like carboxy-protecting groups.

The term NH protecting group refers to amine-protecting groups used to temporarily protect the nitrogen of the β-lactam ring during preparataion or subsequent reactions. The protecting group $R_3$ can arise by virtue of the group being the amine portion of the imine used in the 2+2 cycloaddition, or it may be introduced after removal of such groups. Examples of $R_3$ protecting groups are benzyl, 4-methoxybenzyl, 4-methoxyphenyl or trialkylsilyl, e.g. trimethylsilyl and t-butyldiethylsilyl.

When $R_3$ is protected carboxymethyl, examples of such groups are given hereinabove. This $R_3$ group arises from the ester of glycine used as the amine of the imine in the 2+2 cycloaddition.

Examples of ketal or thioketal derivatives of 1-(protected carboxy)-2-propanone groups, $R_3$, are represented by the formula

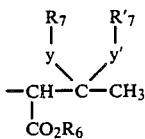

wherein $R_6$ is a carboxy-protecting group, y and y' are oxygen or sulfur, and $R_7$ and $R'_7$ are $C_1$-$C_4$ alkyl when taken separately and when taken together with the oxygen or sulfur atom to which they are bonded form a 5- or 6-membered ring. For example, when $R_6$ is ethyl, y and y' are oxygen and $R_7$ and $R'_7$ are ethyl the diethyl ketal designated is represented by the formula

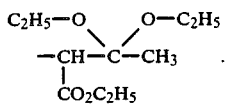

A preferred ketal is the cyclic ketal represented by the formula ($R_7$ and $R'_7$ taken together)

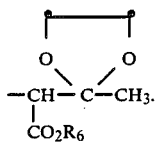

The group $R_2$ in the 4-position of the azetidin-2-one ring arises either directly or indirectly from the aldehyde used in the imine for the 2+2 addition. Examples of such groups are styryl, α-methylstyryl, 2-furylvinyl, 2-methyl-2-furylvinyl, α-naphthylvinyl, m-methoxystyryl, m-(t-butyloxy)styryl, and m-methoxy-α, β-dimethylstyryl, 2-(t-butyloxycarbonyl)ethyl, 2-(benzyloxycarbonyl)ethyl, 2-(4-nitrobenzyloxycarbonyl)ethyl, and the β-keto ester group —CH$_2$CH$_2$COCH$_2$COO-protected, e.g. 4-(t-butyloxycarbonyl)butan-3-one and 4-(4-nitrobenzyloxycarbonyl)butan-3-one. When $R_5$ is protected carboxy, such groups as t-butyloxycarbonyl, benzyloxycarbonyl, and ethoxycarbonyl are exemplary.

The azetidinione of the formula 1 wherein $R_2$ is a 2-(protected-carboxy)ethyl group can be obtained by using 3-(protected-carboxy)propionaldehyde in the formation of the imine used in the cycloaddition reaction. Alternatively, the azetidinone 1 wherein $R_2$ is the group —CH=CH-furfuryl is hydrogenated over palladium catalyst to the group —CH$_2$CH$_2$-furfuryl and the latter is reacted with ozone to form the 2-carboxyethyl substituted azetidinone. The latter is esterified to the ester.

The azetidinone 1 wherein $R_2$ is the β-keto ester group, —CH$_2$CH$_2$—COCH$_2$CO$_2$-protected, can be obtained with the above azetidinone 1 wherein $R_2$ is the 2-carboxyethyl group by known methods, e.g. the malonic acid synthesis. Alternatively, the β-keto ester can be obtained by the method of Evans et al., *Tetrahedron Letters* Vol. 26, No. 32, pp. 3783–3786, 1985. By this method the azetidinone 1 wherein $R_2$ is an m-alkoxystyryl group is reduced catalytically to the corresponding 2-(m-alkoxyphenyl)ethyl group and the latter is reduced to the diene, 2-(3-alkoxycyclohex-1,4-dienyl)ethyl, with lithium-liquid ammonia. Ozonolysis of the diene affords the β-keto ester group $R_2$.

The chiral auxiliary oxazolidinone or imidazolidinone represented by the formula A is obtained with an α-hydroxyacid or α-aminoacid, respectively. The imidazolidinone A is prepared by converting the α-aminoacid to an amino-protected amide and then condensing the amide with an aldehyde R$_1$CHO. For example, phenylglycine is reacted with benzyloxycarbonyl chloride to form the N-Cbz-protected phenylglycine. The latter is converted to the acid amine and the protected amino amide is reacted with the aldehyde R$_1$CHO in the presence of an acid to form the Cbz-protected imidazolidinone represented by the formula

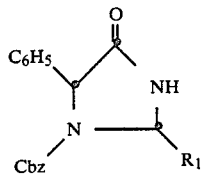

wherein Cbz is benzyloxycarbonyl and $R_1$ is as defined above.

Alternatively, the imidazolidin-4-one ring can be formed by condensing the unprotected α-amino acid amine with the aldehyde R$_1$CHO to form the intermediate imine represented by the formula

The latter on treatment with acid, e.g. methanesulfonic acid or hydrogen chloride, cyclizes to form the imidazolidin-4-one. The 1-position nitrogen of the latter is then protected with a protecting group R', e.g. benzyloxycarbonyl or t-butyloxycarbonyl.

The imidazolidin-4-one is alkylated with a haloacetic acid ester, e.g. t-butyl bromoacetate, to form the compound represented by formula A (Z=NR').

The preparation of the imidazolidinone is illustrated by the following reaction scheme.

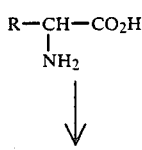

-continued

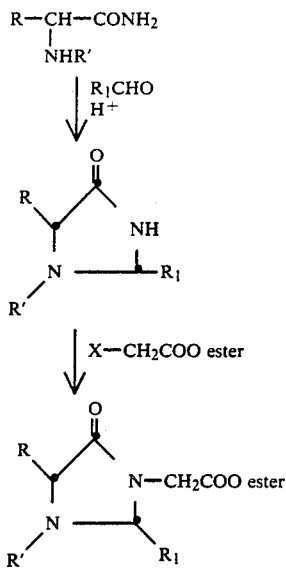

The ester is deesterified and the corresponding acid is converted to the acid chloride for use in the cycloaddition reaction.

The oxazolidinone formula A (Z=O) is obtained as shown below.

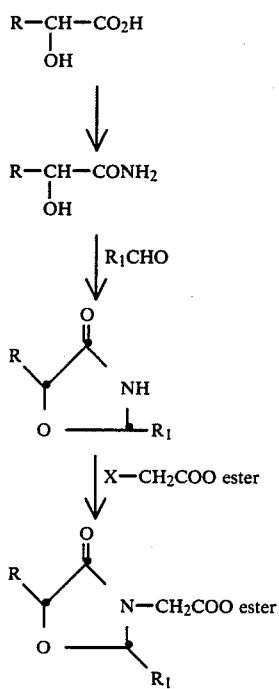

The ester is deesterified and the free acid is converted to the acid chloride with a halogenating agent such as thionyl chloride or oxalyl chloride.

The group R in the formula 1 arises from the α-hydroxy acid or amino acid, respectively, used in the preparation of the oxazolidinone or imidazolidinone as described above. Examples of such α-hydroxy acids are mandelic acid, 4-chloromandelic acid, 3-methoxymandelic acid, α-hydroxyacetic acid, α-hydroxybutyric acid, 4-methylthio-2-hydroxybutyric acid, 3-carbamoyl-2-hydroxypropionic acid, α-(2-naphthyl)-α-hydroxyacetic acid, and α-(1-naphthyl)-α-hydroxyacetic acid. Examples of α-amino-acids are phenylglycine, 4-methoxyphenylglycine, 4-chlorophenylglycine, 3,4-dichlorophenylglycine, 2-naphthylglycine, alanine, leucine, serine, O-methylserine, lysine, valine, norvaline, threonine, S-benzylcysteine, methionine, glutamine and glutamic acid mono ethyl ester.

Examples of $R_1$CHO aldehydes that can be used to prepare the chiral auxiliary are acetaldehyde, propionaldehyde, pivaldehyde, cyclopropyl aldehyde, cyclopentyl aldehyde, cyclohexaldehyde, benzaldehyde, anisaldehyde, 4-chlorobenzaldehyde, tolualdehyde, p-nitrobenzaldehyde, 2,6-dimethylbenzaldehyde, 3-hydroxybenzaldehyde, 4-bromobenzaldehyde, 3-bromo-4-ethylbenzaldehyde, m-cyanobenzaldehyde, 4-carbamoylbenzaldehyde, 1-naphthaldehyde, 2-naphthaldehyde, 4-chloro-2-naphthaldehyde, 8-hydroxy-2-naphthaldehyde, 3-methyl-1-naphthaldehyde, ethyl glyoxalate and t-butyl glyoxalate.

The imine B used in the cycloaddition with the acid chloride is prepared by known methods with the amine $R_3NH_2$ and the aldehyde $R_2$CHO. For example, the amine and aldehyde are mixed together in a water immiscible solvent such as benzene or toluene in the presence of a drying agent, e.g. molecular sieves. Alternatively, the imine is obtained by azeotropic distillation of water from the reaction mixture of the amine and aldehyde. Examples of imines useful in the preparation of the azetidinones 1 are those formed with the amines benzylamine, 4-methoxyaniline and 2,4-dimethoxybenzyl, and the aldehydes cinnamaldehyde, β-(2-furyl)acrolein, β-(α-naphthyl)acrolein, m-methoxycinnamaldehyde, β-(β-naphthyl)acrolein, α,β-dimethylcinnamaldehyde and methyl glyoxalate. The imines formed with the substituted glyinates represented by the formula

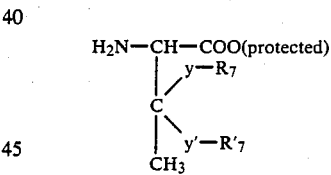

and the $R_2$CHO aldehyde form the azetidinone 1 wherein $R_3$ is a ketal or thioketal derivative of a 1-(protected carboxy)-2-propanone group. A preferred ketal is represented by the above formula wherein the protecting group is t-butyl, y and y' are both oxygen and $R_7$ and $R_7$ are taken together to form the ethylene ketal as represented by the formula

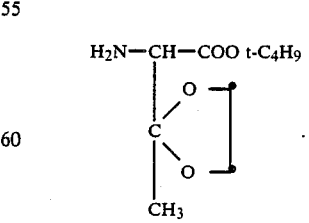

An alternative method for preparing the imine B without proceeding through the amine $R_3NH_2$, comprises the use of an azide as shown in the following scheme.

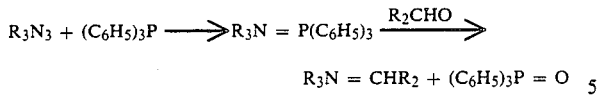

$$R_3N_3 + (C_6H_5)_3P \longrightarrow R_3N = P(C_6H_5)_3 \xrightarrow{R_2CHO}$$
$$R_3N = CHR_2 + (C_6H_5)_3P = O$$

The azide $R_3N_3$ is reacted in an appropriate solvent with a trivalent phosphorous derivative, e.g. triphenylphosphine, or a trialkoxyphosphine to form the intermediate phosphorous ylide. The ylide, without isolation, is reacted with the aldehyde to give the imine and triphenylphosphine oxide. The imine thus obtained can be used directly in the cycloaddition reaction without interference by the phosphine oxide. This method is especially useful where the amine is unstable or difficult to prepare but the azide is available.

The cycloaddition reaction used to form the azetidin-2-one 1 is carried out at temperatures of from about 15° C. to about 35° C. in an inert solvent. The imine and imidazolidinone acetyl chloride or oxazolidinoneacetyl chloride are used in about equimolar amounts, although an excess of either reactant can be used. Preferably, an excess of the imine is used. The reaction proceeds rapidly and, on laboratory scale, is generally over in about an hour or less. The azetidinone product is isolated by conventional methods.

In an example of the preparation, 1-benzyloxycarbonyl-2,5-diphenylimidazolidin-4-one-1-ylacetyl chloride is allowed to react with the imine formed with cinnamaldehyde and p-anisidine in the presence of triethylamine to form the azetidinone, 1-(4-methoxyphenyl)-3-(1-benzyloxycarbonyl-2,5-diphenylimidazolidin-4-one-1-yl)-4-styrylazetidin-2-one.

The imidazolidinone and oxazolidinone chiral auxiliary compounds used in the preparation of the azetidinones 1 provide the cis-azetidinone having the chirality of the natural penicillins and cephalosporins. In the preparation of the chiral auxiliary which has two centers of asymmetry (positions 2 and 5), the chirality of the group at the 2-position controls the chirality of the azetidinone. When the chiral auxiliary is prepared with a D α-amino acid e.g., D-phenylglycine, or a D α-hydroxy acid such as D-mandelic acid, the groups R and $R_1$ of the auxiliary must be trans to each other while if the L-α-amino acid or L-α-hydroxy acid are used, the groups R and $R_1$ must be cis for the tranferance of the correct chirality during the formation of the azetidinone. These cis and trans isomers are illustrated by the formulae

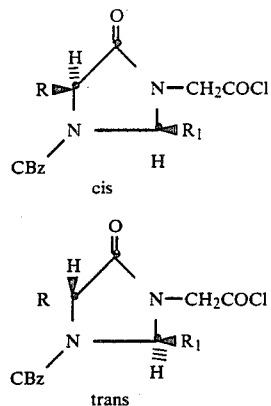

Examples of cis-azetidinones 1 are listed in the following Table wherein the terms have reference to formula 1.

| No. | R | $R_1$ | Z | $R_2$ | $R_3$ |
|---|---|---|---|---|---|
| 1 | phenyl | phenyl | O | styryl | 4-methoxyphenyl |
| 2 | phenyl | phenyl | N—CBz | styryl | 4-methoxyphenyl |
| 3 | phenyl | phenyl | N—CBz | 2-furylvinyl | 4-methoxyphenyl |
| 4 | phenyl | phenyl | N—CBz | protected carboxy | benzyl |
| 5 | 4-chlorophenyl | phenyl | N—CBz | t-butyloxycarbonyl | 4-methoxyphenyl |
| 6 | $C_2H_5$ | phenyl | O | styryl | $t\text{-}C_4H_9OC(O)CH_2-$ |
| 7 | $n\text{-}C_4H_9$ | 4-chlorophenyl | N—CBz | $C_2H_5OC(O)-$ | $C_2H_5OC(O)-CH_2-$ |
| 8 | 4-methoxyphenyl | $t\text{-}C_4H_9$ | N—tBOC | styryl | benzyl |
| 9 | phenyl | phenyl | N—CBz | styryl | $-CH(CO_2C_2H_5)-C-CH_3$ with O O (cyclic) |
| 10 | phenyl | 4-chlorophenyl | N—CBz | 2-furylvinyl | 4-methoxyphenyl |
| 11 | phenyl | 4-chlorophenyl | O | styryl | benzyl |
| 12 | $C_2H_5$ | $C_2H_5$ | O | 3-methoxystyryl | 4-methoxyphenyl |
| 13 | phenyl | phenyl | | | |
| 14 | phenyl | t-butyloxycarbonyl | N—CBz | 2-(2 naphthyl)styryl | $t\text{-}C_4H_9OC(O)CH_2-$ |
| 15 | phenyl | phenyl | NC—Bz | CBz—CH=CH— | 4-methoxyphenyl |
| 16 | phenyl | phenyl | $N-C(O)C_6H_5$ | styryl | 4-methoxyphenyl |

CBz = benzyloxycarbonyl
t-BOC = t-butyloxycarbonyl cis-Azetidinones of the invention (formula 1) wherein the chiral auxiliary moiety is an imidiazolidin-4-one (Z=N—R') are preferred compounds. Especially preferred compounds are represented by the formula 1 wherein Z is N—R', R and $R_1$ are phenyl or substituted phenyl, $R_2$ is a group of the formula $-C(R_4)=C(R_4')R_5$ and wherein R and $R_1$ are trans to each other. A preferred NH-protecting group is the 4-methoxyphenyl group.

Examples of such preferred compounds are 1-(4-methoxyphenyl)-3-(1-benzyloxycarbonyl-2,5-diphenylimidazolidin-4-one-3-yl)-4-styrylazetidin-2-one, 1-(4-methoxyphenyl)-3-[1-(4-nitrobenzyloxycarbonyl)2,5-di-(4-chlorophenyl)imidazolidin-4-one-3-yl]-4-[2-(2-furyl)vinyl]azetidin-2-one, 1-benzyl-3-(1-benzoyl-2,5-diphenylimidazolidin-4-one-3-yl)-4-(t-butyloxycarbonyl)azetidin-2-one, 1-(4-methoxyphenyl)-3-[1-benzyloxycarbonyl-2-(4-chlorophenyl)-5-phenylimidazolidin-4-one-3-yl]-4-(3-methoxystyryl- )azetidin-2-one and 1-(4-methoxyphenyl)-3-[1-benzyloxycarbonyl-2-(t-butyl)-5-phenylimidazolidin-4-one-3-yl]-4-(2-benzyloxycarbonylvinyl)azetidin-2-one.

The azetidinones 1 are useful intermediates for the preparation of antibiotic compounds. For example, the heterocyclic chiral auxiliary in the 3-position of the azetidinone is removed to provide the 3-aminoazetidinone. The azetidinone 1 wherein Z is N—R' first is subjected to hydrolysis or hydrogenolysis to remove the group R'. When R' is $C_1$-$C_4$ alkoxycarbonyl, e.g. t-butyloxycarbonyl, the azetidinone is treated with trifluoroacetic acid to remove the t-BOC group. When R' is benzoyl or substituted benzoyl, the compound is subjected to basic hydrolysis, and when R' is benzyloxycarbonyl or substituted benzyloxycarbonyl, the cleavage is effected by hydrogenolysis, e.g. with palladium on carbon catalyst in an atomosphere of hydrogen.

The des-R azetidinone is then hydrolyzed with base to provide the 3-α-aminoacylaminoazetidinone represented by the formula

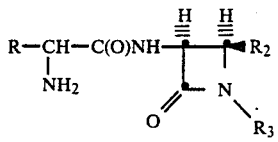

The 3-acyl group, wherein the amino group is protected, is then removed by the well-known N-deacylation-process employed for the N-deacylation of cephalosporins and penicillins. For example, the N-acyl compound is treated with an imino chloride forming reagent such as $PCl_5$, and the imino chloride is converted to the imino ether with a lower alcohol such as methyl alcohol or isobutyl alcohol. The imino ether is then decomposed by hydrolysis to the 3-aminoazetidinone.

The compound 1 wherein Z is oxygen can be hydrolyzed to the α-hydroxyacylamino azetidinone and the latter deacylated following protection of the hydroxy group to the 3-aminoazetidinone by the same deacylation procedure.

The compound 1 wherein $R_3$ is hydrogen is obtained by the removal of the NH-protecting group $R_3$. For example, the preferred NH-protecting group, 4-methoxyphenyl, is removed by treatment of the azetidinone 1 with ceric ammonium nitrate in acetonitrilewater at 0° C. according to the procedure of Guanti et al., *Synthesis*, 1985, pp. 609–611.

The benzyl NH-protecting group can be removed via lithium ammonium reduction.

The azetidinone 1 can be converted to the monobactam type antibiotices, the 3-substituted-1-carba-3-cephem-4-carboxylic acid antibiotics, as well as other types of antibiotics, see for example D. A. Evans and E. B. Sjogren, *Tetrahedron Letters*, Vol. 26, No. 32, pp. 3783–3786, 1985, ibid pp. 3787–3790; Hatanaka et al., *Tetrahedron Letters*, Vol. 24, No. 44, pp. 4837–4838 (1983).

The following Examples further describe the invention.

PREPARATION 1

1-Benzyloxycarbonyl-2,5-diphenylimidazolidin-4-one-3-ylacetic acid

D-Phenylglycine (100 g) was dissolved in 500 ml of acetone containing 1N sodium hydroxide and one equivalent of benzyloxycarbonyl chloride was added dropwise to the solution. During addition the pH was maintained above about 8 with 2N sodium hydroxide. The reaction mixture was extracted with diethyl ether, acidified to pH 1 and extracted with methylene chloride. The extract was dried and evaporated to dryness to yield a solid residue. The residue was triturated with diethyl ether to provide 144 g (71% yield) of N-benzyloxycarbonyl D-phenylglycine as a white crystalline solid.

NMR ($CDCl_3$); δ5.0 (s, 2H), 5.3 (d, J=4 Hz, 1H), 5.7 (d, J=4 Hz, 1H), 7.3 (s, 10H).

$\alpha_D$ −107.2° ($CH_3OH$)

$\alpha_{365}$ −399.6°

The product (142 g) was dissolved in 2 liters of acetonitrile containing 100 ml of dimethylformamide and 70 g of hydroxybenztriazole were added. The mixture was warmed until solution was obtained. Dicyclohexylcarbodiimide (103 g) was added to the solution and the solution was stirred for 30 minutes. The precipitate was filtered and 70 ml of ammonium hydroxide were added to the solution. The reaction mixture was stirred, filtered to remove the precipitate, and evaporated under vacuum. The residue was dissolved in ethyl acetate and the resultant solution was washed twice with a solution of sodium bicarbonate. When the product began to cystallize during washing, diethyl ether was added to the organic layer which was separated, cooled and filtered. The filtrate was evaporated under vacuum and the residue triturated with diethyl ether to yield N-benzyloxycarbonyl D-phenylglycine amide as a solid.

NMR ($CDCl_3$): δ4.8 (s, 2H), 5.0 (d, J=4 Hz, 1H), 6.6 (d, J=4 Hz, 1H), 7.0 (s, 10H).

$\alpha_D$ −7°

$\alpha_{365}$ −25.8°

Mass spectrum M+ 284.

The Cbz-protected amide product (1.42 g), benzaldehyde (2 g) and 950 mg of p-toluenesulfonic acid were dissolved in 50 ml of 1,1,2-trichloroethane and the solution was he ated at the reflux temperature for 16 h. The reaction mixture was cooled and washed with aqueous sodium bicarbonate. The reaction mixture was chromatographed via silica preparative plate chromatography to yield two isomers A and B 1-benzyloxycarbonyl-2,5-diphenylimidazolidin-4-one. The isomers has a mass ion of M+ 372.

Isomer A: $\alpha_D$ −60°

NMR ($CDCl_3$): δ4.8 (q, 2H), 5.24 (pair doublets, J=1 Hz, 1H), 6.8 (pair doublets, J=1 Hz, 1H), 6.7-7.4 (m, 10H).

Isomer B: $\alpha_D$ −162.7°

$\alpha_{365}$ −622.6° C.

NMR ($CDCl_3$): δ5.0 (s, 2H), 5.2 (s, 1H), 6.4 (s, 1H), 7.0-7.3 (m, 10H).

Isomer B (7.16 g) was dissolved in 200 ml of THF and sodium hydride (960 mg of 50% dispersion in oil) was added at room temperature. After stirring for 30 min. 3.31 ml of t-butyl bromoacetate were added and the reaction mixture was stirred at room temperature for 16 h. The mixture was evaporated to remove the solvent and a mixture of dilute hydrochloric acid and diethyl ether was added. The ether was evaporated, the yellow oil obtained was dissolved in trifluoroacetic acid and the mixture was stirred for 1 h. The excess trifluoroacetic acid was removed under vacuum, diethyl ether was added to the residue and the solution was extracted twice with aqueous sodium bicarbonate. The aqueous bicarbonate extracts were combined, acidified, and the product extracted twice with methylene chloride. The extracts were combined, dried and evaporated under vacuum to yield the title compound as a white foam.

Mass spectrum: M+ 430

$\alpha_D - 5°$ $\alpha_{365} - 21°$

NMR (CDCl$_3$): δ3.22 (d, J=9 Hz, 1H), 4.44 (d, J=9 Hz, 1H), 5.0 (s, 2H), 5.42 (s, 1H), 6.2 (s, 1H), 6.9-7.4 (m, 10H).

PREPARATION 2

1-Benzoyl-2-(t-butyl)-5-phenylimidazolidin-4-one-3-ylacetic acid

To a solution of 56.5 g of thionyl chloride in 300 ml of methyl alcohol cooled to −5° C. were added 107.5 g of D-phenylglycine and the mixture was heated at the reflux temperature for 2 h. The mixture was evaporated under vacuum to remove the alcohol, the residue was dissolved in water and the pH of the solution was adjusted to 7.4 with 2N sodium hydroxide. The solution was extracted with diethyl ether, the extract dried and evaporated to provide 78 g of methyl D-phenylglycinate as a yellow oil.

The methyl ester (5 g) was dissolved in 25 ml of methylene chloride and the solution was cooled to −5° C. Ammonia was bubble through the solution for 3 days as the temperature was maintained at 0° C. The mixture was evaporated under vacuum at 60° C. to provide the D-phenylglycine amide as a white solid. The solid was triturated with diethyl ether and filtered. The solid showed $\alpha_D - 106°$, $\alpha_{365} - 380°$.

The product was recrystallized from ethyl acetate-diethyl ether to yield 3.2 g of the amide: $\alpha_D - 111°$, $\alpha_{365} - 395°$.

The amide (3.2 g) was added to 100 ml of benzene containing 3 ml of pivalaldehyde and the mixture was heated at the reflux temperature under a Dean-Stark trap until a clear solution ws obtained. The solution was evaporated under vacuum to yield a white solid residue of the pivalaldehyde imine formed with the phenylglycide amide represented by the formula (CH$_3$)$_3$C—C=N—CH(C$_6$H$_5$)CONH$_2$.

$\alpha_D - 109°$, $\alpha_{365} - 389°$.

NMR (CDCl$_3$): δ4.8 (s, 1H) 7.2-7.9 (m, 5H), 8.22 (s, 1H).

The imine was dissolved in 50 ml of methyl alcohol, the solution cooled to −5° C. and hydrogen chloride was bubbled through the cold solution for 10 min. The solution was then stirred at −5° C. for 30 min. and at room temperature for 4 h. The white crystalline precipitate which formed was filtered to provide 2.65 g of 2-(t-butyl)-5-phenylimidazolidin-4-one, isomer A, hydrochloride, $\alpha_D + 46°$, $\alpha_{365} + 168°$.

NMR (CDCl$_3$): δ0.9 (s, 9H), 2.22 (s, 1H), 4.41 (d, J=1 Hz, 1H), 4.55 (d, J=1 Hz, 1H), 7.3 (s, 5H), 8.24 (s, 1H).

The filtrate was stirred for 16 h. at room temperature, the solvent evaporated off under vacuum, and diethyl ether was added to the residue to provide 2.45 of isomer B as a white solid. The solid was a mixture of isomers of the product. Thin layer chromatography showed A to be less polar than B. The B fraction was contaminated with a minor amount of A. The fractions A and B were separated chromatographically on silica gel to provide A as 2.25 g (foam), $\alpha_D - 63°$, $\alpha_{365} 247°$; and isomer B as 2.2 g (white solid), $\alpha_D 100°$, $\alpha_{365} - 397°$.

Isomer A hydrochloride salt (2.54 g) was dissolved in 100 ml of methylene chloride, 3.2 ml of triethylamine were added, the solution cooled to 0° C. and 1.39 ml of benzoyl chloride were added with stirring. The reaction mixture was stirred for 16 h at room temperature, evaporated, and the residue dissolved in ethyl acetate/dilute aqueous sodium bicarbonate. The organic layer was separated, washed with dilute hydrochloric acid, dried and evaporated. The residue was crystallized from diethyl ether-hexane to yield 1.2495 of 1-benzoyl-2-(t-butyl)-5-phenylimidazolidin-4-one as white crystals.

$\alpha_D - 163°$ $\alpha_{365} - 677°$

NMR (CDCl$_3$): δ1.03 (s, 9H), 5.0 (s, 1H), 5.80 (s, 1H), 6.7-7.3 (m, 10H), 8.27 (s, 1H).

The 1-benzoyl derivative, 322 mg, was dissolved in 20 ml of THF, the solution cooled to −78° C. and 1.1 eq of n-butyllithium (0.7 mls of 1.6N) were added with stirring. The mixture was stirred for 5 min. at −78° C. and 195 mg of t-butyl bromacetate were added. After 1 h. the t-butyl 1-benzoyl-2-(t-butyl)-5-phenylimidazolidin-4-one-3-ylacetate was recovered from the reaction mixture by extraction with ethyl acetate.

The above alkylation was repeated with 500 mg of the 1-benzoyl derivative melting at about 167° C. (C$_2$H$_5$OH).

$\alpha_D - 106°$ $\alpha_{365} - 443°$

NMR (CDCl$_3$): δ1.04 (s, 9H), 1.47 (s, 9H), 3.80 (d, J=18 Hz, 1H), 4.60 (d, J +18 Hz, 1H), 5.02 (s, 1H), 6.01 (s, 1H), 6.8-7.2 (m, 10H).

The ester was treated with trifluoroacetic acid at room temperature for 0.5 h to form the title compound 1-benzoyl-2-(t-butyl)-5-phenylimidazolidin-4-one-3-ylacetic acid.

NMR (CDCl$_3$): δ1.15 (s, 9H), 4.0 (d, J=18 Hz, 1H), 4.70 (d, J=18 Hz, 1H), 5.2 (s, 1H), 6.02 (s, 1H), 6.8-7.2 (m, 10H).

PREPARATION 3

1-Benzyloxycarbonyl-2-(2,5-dimethylphenyl)-5-phenylimidazolidin-4-one

A solution of 2.84 g of N-benzyloxycarbonyl D-phenylglycine amide in 100 ml of toluene was treated with 2.7 g of 2,5-dimethylbenzaldehyde and 0.5 ml of methanesulfonic acid and the mixture was heated at the reflux temperature for 24 h. The reaction mixture was evaporated and the product was isolated by preparative HPLC (silica). There were obtained the two isomeric imidazolidinones represented by the formulae

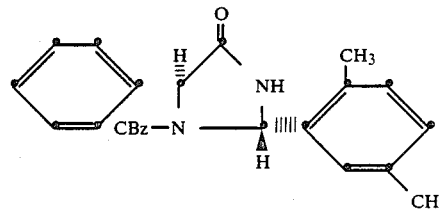

B

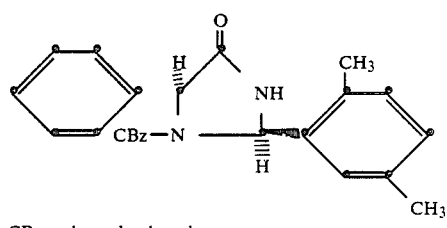

A

CBz = benzylcarbonyl

A. NMR (CDCl₃): δ2.27 (s, 3H), 2.4 (s, 3H), 4.72 (d, J=12 Hz, 1H), 4.86 (d, J=12 Hz, 1H), 5.38 (d, 1H), 6.5 (d, 1H), 6.6 (m, 2H), 7.0–7.4 (m, 11H).

B. NMR (CDCl₃): δ2.17 (s, 6H), 5.01 (s, 2H), 5.32 (s, 1H), 6.40 (s, 1H), 6.8–7.5 (m, 13H).

PREPARATION 4

1-Benzyloxycarbonyl-2-(4-bromophenyl)-5-phenylimidazolidin-4-one

The title compound was obtained with 4-bromobenzaldehyde and the CBz-protected D-phenylglycine amide by following the procedures of the foregoing preparations. There were obtained via preparative HPLC (silica) two isomeric imidazolidinones represented by the formulae

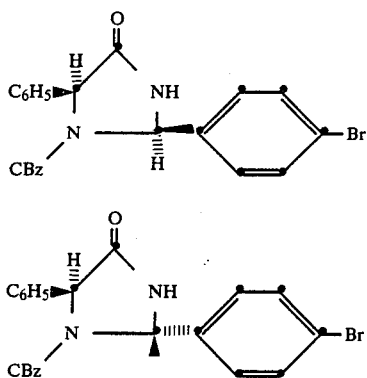

A. NMR (CDCl₃): δ4.7 (d, J=12 Hz, 1H), 4.93 (two d, J=12 Hz, 1H), 5.2 and 5.3 (s, 1H), 6.1 and 6.2 (s, 1H).

B. NMR (CDCl₃): δ5.05 (s, 2H), 5.27 (s, 1H), 6.20 (s, 1H), 6.8–7.6 (m, 14H).

PREPARATION 5

1-Benzyloxycarbonyl-2-cyclopentyl-5-phenylimidazolidin-4-one

A solution of 1.5 g of D-phenylglycine amide and 1.3 ml of cyclohexyaldehyde in 50 ml of benzene was refluxed under a Dean Stark water trap for 0.5 h. The mixture was evaporated under vacuum to give the imine amide represented the the formula

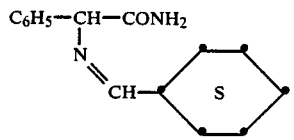

The imine was dissolved in 25 ml of methyl alcohol and 25 ml of methyl alcohol saturated with hydrogen chloride (saturated at 0° C.) was added to the solution. The solution was stirred at room temperature for 16 h. The white crystals were filtered to provide 210 mg of product. The filtrate was evaporated to dryness under vacuum to a white residue which on trituration with diethyl ether gave 2.6 g of the product as a white solid.

The above preparation was repeated on a larger scale (4.5 g of D-phenylglycine amide) and the products combined with those of the run above. Two major isomeric products of the reaction, represented by the formula below, were separated by preparative HPLC with ethyl acetate

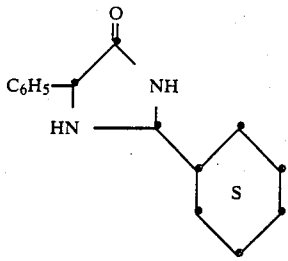

Product A $\alpha_D - 16°$

NMR (CDCl₃): δ1.0–2.0 (m, 11H), 4.4 (q, J=3 Hz, 1 Hz, 1H), 4.5 (d, J=1 Hz, 1H), 7.2–7.4 (m, 5H).

Product B $\alpha_D - 43°$

NMR (CDCl₃): δ1.0–2.0 (m, 11H), 4.44 (d, J=3 Hz, 1H), 4.6 (s, 1H), 7.2–7.6 (m, 5H).

PREPARATION 6

1-Benzloxycarbonyl-2-(4-methoxyphenyl)-5-phenylimidazolidin-4-one

To a solution of 2 g of N-Cbz-protected D-phenylglycine amide in 100 ml of toluene were added 1.5 g of 4-methoxybenzaldehyde and 1 ml of methanesulfonic acid and the solution was heated at the reflux temperature for 4 h. The mixture was evaporated to dryness under vacuum and diethyl ether was added to the residue. The title compound was obtained (2.3 g white crystals).

$\alpha_D - 82°$ $\alpha_{365} - 322°$

NMR (CDCl₃): δ3.75 (s, 3H), 5.0 (s, 2H), 5.2 (s, 1H), 6.1 (s, 1H), 6.7–7.4 (m, 14H).

PREPARATION 7

1-Benzyloxycarbonyl-2-(1-naphthyl)-5-phenylimidazolidin-4-one

The title compound was obtained as two isomers with 1-naphthaldehyde and N-Cbz D-phenylglycine amide by the procedure used in the foregoing preparations. The isomers were separated by preparative HPLC.

cis isomer: $\alpha_D - 130°$ $\alpha_{365} - 456°$

NMR (CDCl₃): δ4.55 (q, 2H), 5.26 (br.d, 1H), 6.2–6.6 (two br.d, 1H), 6.8–8.4 (m, 17H).

trans isomer: $\alpha_D - 69°$ $\alpha_{365} - 294°$

NMR (CDCl₃): δ5.0 (s, 2H), 5.32 (s, 1H), 6.90 (s, 1H), 6.9–8.1 (m, 17H).

EXAMPLE 1

1-(4-Methoxyphenyl)-3-(1-benzyloxycarbonyl-2,5-diphenylimidazolidin-4-one-1-yl)-4-styrylazetidin-2-one To a solution of 1.78 g of 1-benzyloxycarbonyl-2,5-diphenylimidazolidin-4-one-1-ylacetic acid (isomer A prepared as described in Preparation 1) in 25 ml of methylene chloride were added 0.39 ml of oxalyl chloride and 6 drops of dimethylformamide (DMF). The reaction mixture was stirred at room temperature for about 0.75 h. to provide a solution of the corresponding acid chloride.

The solution was mixed with a solution of 1 g of the imine (formed with cinnamaldehyde and 4-methoxyaniline) and containing 0.42 g of triethylamine. On stirring at room temperature the product (represented by the formula below) precipitated rapidly and was filtered to yield 1.85 g of white crystals (69% yield). There were obtained 110 mg of a second crop of the product from the filtrate.

$\alpha_D$(DMSO)+10°
$\alpha_{365}$ +14°

NMR (DMSOd$_6$): δ3.64 (s, 3H), 4.48 (d, J=4 Hz, 1H), 4.72 (s, 2H), 5.0 (q, J=4 Hz, 6 Hz, 1H), 5.62 (s, 1H), 5.9 (q, J=6 Hz, 8 Hz, 1H), 6.22 (s, 1H), 6.5 (d, J=8 Hz, 1H), 6.8–7.5 (m, 19H).

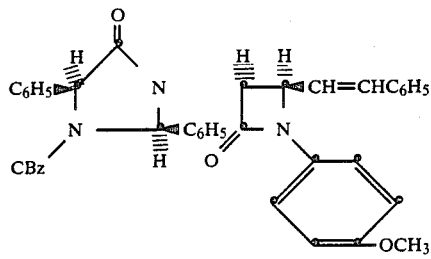

EXAMPLE 2

1-(4-Methoxyphenyl)-3-(1-benzyloxycarbonyl-2,5-diphenylimidazolidin-4-one-1-yl)-4-styrylazetidin-2-one To a solution of 4.3 g of 1-benzyloxycarbonyl-2,5-diphenylimidazolidin-4-one-1-ylacetic acid, isomer B, in 100 ml of methylene chloride was added 0.94 ml of oxalyl chloride and 6 drops of DMF and the solution was stirred at room temperature for 1 h.

The solution of the acid chloride was evaporated to dryness under vacuum and the residue dissolved in 20 ml of methylene chloride. The solution was added to a solution of 2.37 g of the imine (formed with cinnamaldehyde and 4-methoxyaniline) in 100 ml of methylene chloride containing 1.44 ml of triethylamine. The reaction mixture was stirred at room temperature for 1 h., was evaporated under vacuum to remove the solvent and the residue dissolved in ethyl acetate. The solution was washed with dilute aqueous sodium bicarbonate, dilute hydrochloric acid, was dried and evaporated to dryness under vacuum. The residue was triturated with methyl alcohol and the product represented by the formula below crystallized.

The white solid was filtered to yield 4.63 g of the product after air drying. A second crop, 0.39 g, of the product was obtained from the filtrate (77% yield).

Mass spectrum: M+ 649.

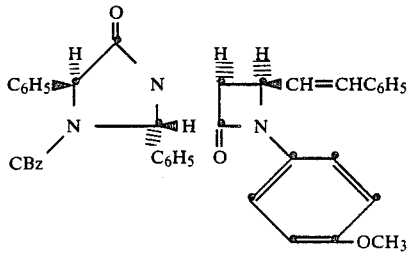

NMR (CDCl$_3$): δ3.64 (s, 3H), 4.58 (d, J=4 Hz, 1H), 4.90 (q, J=4 Hz, 6 Hz, 1H), 4.92 (s, 2H), 5.22 (s, 1H), 6.1 (s, 1H), 6.6–7.5 (m, 21H).

EXAMPLE 3

1-(4-Methoxyphenyl)-3-(1-benzyloxycarbonyl-2,5-diphenylimidazolidin-4-one-1-yl)-4-ethoxycarbonylazetidin-2-one In following the procedures described in Example 2, 1-benzyloxycarbonyl-2,5-diphenylimidazolidin-4-one-1-ylacetic chloride (isomer B) is condensed in the presence of triethylamine with the imine formed with p-anisidine and ethyl glyoxalate to provide the title compound represented by the formula

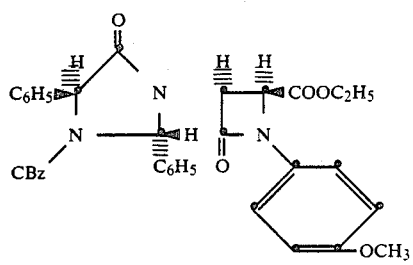

EXAMPLE 4

1-(4-Methoxyphenyl)-3-[1-benzoyl-2-(t-butyl)-5-phenylimidazolidin-4-one-3-yl)-4-styrylazetidin-2-one To a solution of 380 mg of 1-benzoyl-2-(t-butyl)-5-phenylimidazolidin-4-one-3-ylacetic acid (prepared as described by Preparation 2) in 20 ml of methylene chloride were added 127 mg of oxalyl chloride and 3 drops of DMF. The mixture was stirred at room temperature for 0.5 h and then was evaporated under vacuum to provide the corresponding acid chloride.

The acid chloride was dissolved in 25 ml of methylene chloride, the solution cooled to −78° C. and 0.22 ml (1.5 eq) of triethylamine were added. The mixture was stirred for 15 min. before a solution of 237 mg of the imine (prepared with anisidine and cinnamaldehyde) in 10 ml of methylene chloride was added. The mixture was stirred for 15 min. at −78° C. and at room temperature for 3 h. The mixture was washed with dilute hydrochloric acid and dilute aqueous sodium bicarbonate, was dried and evaporated. The residue was triturated with diethyl ether to give 239 mg of the title compound, white crystals (42% yield), as one isomer represented by the formula

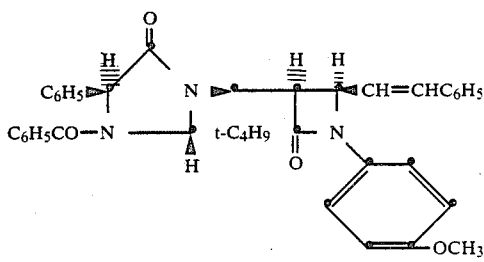

Mass Spectrum: M+ 599
IR 1756, 1720, 1647 cm$^{-1}$
$\alpha_D$ −107°
$\alpha_{365}$ −692°

NMR (CDCl₃): 1.3 (s, 9H), 3.73 (s, 3H), 5.03 (q, J=5 Hz, J=9 Hz, 1H), 5.1 (s, 1H), 5.2 (d, J=5 Hz, 1H), 5.98 (s, 1H), 6.14 (q, J=9 Hz, 15H), 6.78 (d, J=8 Hz, 2H), 6.85 (d, J=15 Hz, 1H), 7.0–7.3 (m, 15H), 7.38 (d, J=8 Hz, 2H).

EXAMPLE 5

1-(4-Methoxyphenyl)-3-[1-benzyloxycarbonyl-2-(4-methoxyphenyl)-5-phenylimidazolidin-4-one-3-yl]-4-styrylazetidin-2-one The 1-Cbz-protected imidazolidinone prepared as described by Preparation 6 was alkylated with t-butyl bromoacetate and the t-butyl ester removed by treatment with TFA to give trans-1-benzyloxycarbonyl-2-(4-methoxyphenyl)-5-phenylimidazolidin-4-one-3-ylacetic acid as the major product. The minor product was the cis isomer.

The trans acid, 1.31 g was dissolved in 50 ml of methylene chloride, 6 drops of DMF and 0.3 ml of oxalyl chloride was added. After stirring at room temperature for 1 h the solution was evaporated under vacuum for 0.5 h to remove excess oxalyl chloride. The residue was then dissolved in 50 ml of fresh methylene chloride, the solution cooled to −78° C., 0.6 ml of triethylamine was added and the solution was stirred at −78° C. for 15 min. The enamine formed with anisidine and cinnamaldehyde (200 mg in 10 ml of CH₂Cl₂) was added and the mixture after warming to room temperature was stirred for 2 h. The mixture was washed with dilute HCl and dilute aqueous NaHCO₃. TLC showed 1 major spot. The product was purified by preparative HPLC to give 1.393 g of one isomer as the major product.

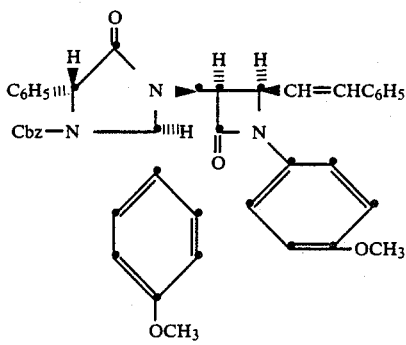

Mass Spectrum: M⁺ 679
$\alpha_D$ −15° C.
$\alpha_{365}$ − 195°
NMR (CDCl₃): δ3.7 (s, 3H), 3.76 (s, 3H), 4.7–4.8 (m, 2H), 5.0 (s, 2H), 5.33 (s, 1H), 6.20 (s, 1H), 6.6–7.4 (m, 20H).

I claim:
1. The compound of the formula

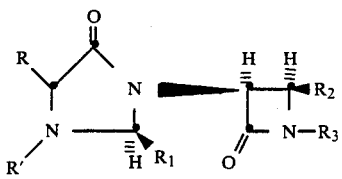

wherein R' is $C_1$–$C_4$ alkoxycarbonyl, benzyloxycarbonyl, Ar-substituted benzyloxycarbonyl substituted by one or two of the same or different groups selected from $C_1$–$C_4$ alkoxy, halogen, cyano, nitro, amino, mono- or di-($C_1$–$C_4$ alkyl)amino, carbamoyl or hydroxy; benzoyl or benzoyl substituted by one or two of the same or different groups selected from $C_1$–$C_4$ alkyl, $C_1$–$C_4$ alkoxy, halogen, hydroxy, cyano, carbamoyl, amino, mono- or di-($C_1$–$C_4$ alkyl)amino, $C_1$–$C_4$ alkylsulfonylamino or nitro.

R is $C_1$–$C_4$, $C_1$–$C_4$ alkyl mono-substituted by hydroxy, protected carboxy, carbamoyl, $C_1$–$C_4$ alkylthio; or protected amino; phenyl, substituted pheyl substituted by one or two of the same or different groups selectedfrom $C_1$–$C_4$ alkyl, $C_1$–$C_4$ alkoxy, halogen, hydroxy, cyano, carbamoyl, amino, mono- or di-($C_1$–$C_4$ alkyl)amino, $C_1$–$C_4$ alkylsulfonylamino or nitro; napthyl, substituted naphythyl substituted by one or two of the same or different groups selected from $C_1$–$C_4$ alkyl, $C_1$–$C_4$ alkoxy, halogen, cyano, nitro, amino, mono- or di-($C_1$–$C_4$ alkyl)amino, carbamoyl or hydroxy; or $C_1$–$C_4$ alkoxycarbonyl;

$R_1$ is $C_1$–$C_4$ alkyl, $C_3$–$C_7$ cycloalkyl, phenyl, substituted phenyl as defined above, naphthyl, substituted naphthyl as defined above or $C_1$–$C_4$ alkoxycarbonyl;

$R_2$ is $C_1$–$C_4$ alkoxycarbonyl, 2-(protected carboxy)ethyl, 4-(protected carboxy)butan-3-one or a group of the formula

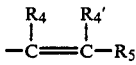

wherein $R_4$ and $R_4'$ independently are hydrogen or $C_1$–$C_4$ alkyl and $R_5$ is phenyl, naphthyl, $C_1$–$C_4$ alkoxyphenyl, furyl or protected carboxy; and $R_3$ is hydrogen, protected carboxymethyl, a ketal of thioketal of the formula

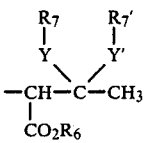

wherein $R_6$ is a carboxy-protecting group; Y and Y' are both O or S, and $R_7$ and $R_7'$ when taken separately are $C_1$–$C_4$alkyl and when taken together are —CH₂CH₂— or —CH₂—CH₂—CH₂— which, with the O or S atoms to which they are bonded, form a 5- or 6-membered ring, respectively; or $R_3$ is an NH-protecting group.

2. The compound of claim 1, wherein $R_2$ is 2-(protected carboxy)ethyl or 4-(protected carboxy)butan-3-one, and $R_3$ is hydrogen.

3. The compound of claim 2 wherein R is phenyl or substituted phenyl and $R_1$ is $C_1$–$C_4$ alkyl, phenyl or, substituted phenyl.

4. The compound of claim 1 wherein R' is benzyloxycarbonyl or an Ar-substituted benzyloxycarbonyl.

5. The compound of claim 1 wherein R and $R_1$ are phenyl or substituted phenyl.

6. The compound of claim 1 wherein $R_3$ is 4-methoxyphenyl.

7. The compound of claim 1 wherein $R_2$ is a group of the formula

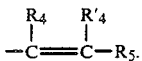

8. The compound of claim 1 wherein $R_2$ is $C_1$–$C_4$ alkoxycarbonyl.

9. The compound of claim 7 which is 1-(4-methoxyphenyl)-3-(1-benzyloxycarbonyl-2,5-diphenylimidazolidin-4-one-3-yl)-4-styrylazetidin-2-one.

10. The compound of claim 7 which is 1-(4-methoxyphenyl)-3-(1-benzyloxycarbonyl-2,5-diphenyl-imidazolidin-4-one-3-yl)-4-[2-(2-furyl)vinyl]azetidin-2-one.

11. The compound of claim 1 wherein R' is benzoyl or substituted benzoyl.

12. The compound of claim 11 which is 1-(4-methoxybenzyl)-3-(1-benzoyl-2-t-butyl-5-phenylimidazolidin-4-one-3-yl)-4-styrylazetidin-2-one.

13. The compound of claim 1 wherein $R_3$ is hydrogen.

14. The compound of claim 3 wherein R and $R_1$ are phenyl and $R_2$ is 2-(t-butyloxycarbonyl)ethyl.

15. The compound of claim 13 wherein $R_2$ is a group of the formula

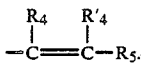

16. The compound of claim 15 wherein R' is benzyloxycarbonyl, R and $R_1$ are phenyl or substituted phenyl, and $R_5$ is phenyl, m-alkoxyphenyl, furyl or protected carboxy.

* * * * *